United States Patent
Bahn et al.

(10) Patent No.: US 9,267,034 B2
(45) Date of Patent: Feb. 23, 2016

(54) POLYORGANOSILOXANE COMPOUND, METHOD FOR PREPARING THE SAME, AND COPOLYCARBONATE RESIN COMPRISING THE SAME

(71) Applicant: LG CHEM, LTD., Seoul (KR)

(72) Inventors: Hyong Min Bahn, Daejeon (KR); Moo Ho Hong, Daejeon (KR); Young Young Hwang, Daejeon (KR); Min Jeong Kim, Daejeon (KR); Jung Jun Park, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 14/635,668

(22) Filed: Mar. 2, 2015

(65) Prior Publication Data

US 2015/0315380 A1 Nov. 5, 2015

Related U.S. Application Data (63) Continuation of application No. PCT/KR2014/005836, filed on Jul. 1, 2014.

(30) Foreign Application Priority Data

| Jul. 1, 2013 | (KR) | 10-2013-0076439 |
| Jul. 1, 2013 | (KR) | 10-2013-0076449 |
| Jun. 30, 2014 | (KR) | 10-2014-0080436 |
| Jun. 30, 2014 | (KR) | 10-2014-0080439 |

(51) Int. Cl.
*C08G 77/18* (2006.01)
*C08L 69/00* (2006.01)

(52) U.S. Cl.
CPC .............. *C08L 69/00* (2013.01); *C08G 77/18* (2013.01); *C08L 2201/10* (2013.01)

(58) Field of Classification Search
None
See application file for complete search history.

(56) References Cited

U.S. PATENT DOCUMENTS

| 4,241,011 A | | 12/1980 | Hirozawa et al. | |
| 5,130,460 A | * | 7/1992 | Kamei et al. | 556/449 |
| 5,243,009 A | * | 9/1993 | Rich et al. | 528/26 |
| 5,552,506 A | * | 9/1996 | Ebbrecht et al. | 528/15 |
| 5,631,330 A | | 5/1997 | Yezrielev et al. | |
| 5,726,271 A | * | 3/1998 | Furukawa et al. | 528/29 |
| 5,932,677 A | | 8/1999 | Hoover et al. | |

(Continued)

FOREIGN PATENT DOCUMENTS

| JP | 8-73882 A | 3/1996 |
| JP | 10204179 | 8/1998 |
| JP | 3195848 | 8/2001 |
| JP | 3285951 B2 | 5/2002 |
| JP | 4525881 | 8/2010 |
| JP | 2013-503247 A | 1/2013 |
| KR | 1020020016922 | 3/2002 |
| KR | 1020120050968 | 5/2012 |
| KR | 1020120098769 | 9/2012 |
| KR | 10-2013-0047332 A | 5/2013 |
| WO | 2013058214 | 4/2013 |

OTHER PUBLICATIONS

"Synthesis and Characterization of High-Performance Epoxy Resin Based on Disiloxane and 4,40-Oxybis(benzoic acid) Ester" Wang, et al.; Journal of Applied Polymer Science, vol. 123,2485-2491 (2012).

*Primary Examiner* — Robert S Loewe
(74) *Attorney, Agent, or Firm* — Dentons US LLP (57) ABSTRACT

A polyorganosiloxane compound, a method of preparing the same, and a copolycarbonate resin comprising the same are disclosed. Particularly, a copolycarbonate resin, which may be applied to a variety of applications, and in particular, comprises a polyorganosiloxane compound used as an impact modifier, a modifier, or a comonomer of a copolycarbonate resin and has improved mechanical properties such as low-temperature impact strength, is disclosed.

18 Claims, 4 Drawing Sheets

(56) References Cited

U.S. PATENT DOCUMENTS

| | | | |
|---|---|---|---|
| 6,630,562 B2 * | 10/2003 | Ogawa et al. | 528/196 |
| 7,232,865 B2 * | 6/2007 | DeRudder et al. | 525/446 |
| 7,888,447 B2 | 2/2011 | Dhara et al. | |
| 2005/0187372 A1 | 8/2005 | Venderbosch et al. | |
| 2012/0252961 A1 * | 10/2012 | Sybert et al. | 524/537 |
| 2012/0283378 A1 * | 11/2012 | Shoshi et al. | 524/556 |

* cited by examiner

POLYORGANOSILOXANE COMPOUND, METHOD FOR PREPARING THE SAME, AND COPOLYCARBONATE RESIN COMPRISING THE SAME

TECHNICAL FIELD

The present invention relates to a polyorganosiloxane compound, a method for preparing the same, and a copolycarbonate resin comprising the same. More particularly, the present invention relates to a polyorganosiloxane compound which may be applied to a variety of applications, and in particular, may be used as an impact modifier or a modifier or comonomer of a copolycarbonate resin, a method of preparing the same, and a copolycarbonate resin having improved mechanical properties such as low-temperature impact strength by comprising the same and having excellent transparency compared to one having a similar molecular weight.

BACKGROUND ART

Polyorganosiloxane as a kind of silicone means a polymer having a siloxane bond substituted with organic groups as a main chain. For example, it is prepared by polymerization with an aromatic diol such as bisphenol A and a carbonate precursor such as phosgene, which is colorless, odorless, resistant to oxidation, and stable at room temperature, and hypoallergenic insulators. It is used in electronics, vehicles, machines, medicine, cosmetics, lubricants, adhesives, gaskets, artificial aids for plastic surgery, and the like. As a conventional technology, KR Patent publication No. 2002-0016922 (published on Mar. 6, 2002) discloses a polyorganosiloxane that is useful for a material of a hydrogel contact lens, a terminal of which is capped with trimethylsilyl.

In addition, the polyorganosiloxane has superior impact strength, dimensional stability, heat-resistance, transparency, and the like, and is applied to a variety of fields such as claddings of electrical and electronic equipment, vehicle components, materials for construction, optical components, and the like. Recent research into such a copolycarbonate resin has mainly been performed with respect to introducing a monomer having a different structure to a main chain of polycarbonate by polymerizing two or more aromatic diols having different structures, which may be applied to a wider variety of fields, to obtain desired properties.

Particularly, research to introduce a polysiloxane structure to a main chain of polycarbonate is also being performed. However, most technologies have a high production unit cost, transparency and the like is reduced when chemical resistance or impact strength, particularly, low-temperature impact strength, increases, and impact strength and the like are reduced when transparency is improved.

In particular, U.S. Pat. No. 5,932,677 uses eugenol-polydimethylsiloxane to improve low-temperature impact strength, and JP Patent No. 3,195,848 suggests allylphenol-polydimethylsiloxane.

However, such polydimethylsiloxanes have been used to improve low-temperature impact strength while maintaining transparency, but satisfactory transparency has not been provided.

Accordingly, research to improve low-temperature impact strength while maintaining transparency of a copolycarbonate resin as much as possible has been underway.

DISCLOSURE

Technical Problem

The present invention has been made in view of the above problems, and it is one object of the present invention to provide a polyorganosiloxane compound which may be applied in a variety of applications, and in particular, may be used as an impact modifier, a modifier or a comonomer of a copolycarbonate resin, and a copolycarbonate resin comprising the same and having improved low-temperature impact strength while maintaining transparency.

Technical Solution

The present invention provides a polyorganosiloxane compound represented by Formula 1 below:

[Formula 1]

wherein $R_1$, $R_2$, $R_3$, $R'_1$, $R'_2$, and $R'_3$ are independently hydrogen, an alkyl group having a carbon number of 1 to 3, or an aryl group, $R_4$ is $R_4'$ is an alkyl group having a carbon number of 1 to 3, an aryl group, or any one of $R_5$, $R'_5$, and $R_7$ is independently —OH and each of the others is hydrogen, $R_6$ is hydrogen or an alkoxide group having a carbon number of 1 to 4, $R_8$ is a linear or branched alkylene group having a carbon number of 2 to 8, and n and m are integers where $0 < n+m \leq 99$.

Further, the present invention provides a method of preparing a polyorganosiloxane compound, which uses an alkenyl alcohol having a carbon number of 2 to 8 and hydroxybenzoic acid as starting materials, and comprising esterificating the alkenyl alcohol having a carbon number of 2 to 8 with the hydroxybenzoic acid to prepare an alkenyl hydroxybenzoate, and hydrosilylating the alkenyl hydroxybenzoate with H-PDMS, terminal groups in both sides of which are hydrogen, as polyorganosiloxane to prepare a polyorganosiloxane compound represented by Formula 1 below:

[Formula 1]

wherein $R_1$, $R_2$, $R_3$, $R'_1$, $R'_2$, and $R'_3$ are independently hydrogen, an alkyl group having a carbon number of 1 to 3, or an aryl group, $R_4$ is $R'_4$ is an alkyl group having a carbon number of 1 to 3, an aryl group, or any one of $R_5$, $R'_5$, and $R_7$ is independently —OH and each of the others is hydrogen, $R_6$ is hydrogen or an alkoxide group having a carbon number of 1 to 4, $R_8$ is a linear or branched alkylene group having a carbon number of 2 to 8, and n and m are integers where $0<n+m\leq 99$.

Further, the present invention provides a method of preparing a polyorganosiloxane compound, which uses an alkenyl alcohol having a carbon number of 2 to 8 and hydroxybenzoic acid as starting materials, and comprising:

reacting the alkenyl alcohol having a carbon number of 2 to 8 with H-PDMS to obtain OH-PDMS; and adding the hydroxybenzoic acid to the OH-PDMS and then performing esterification in an acid catalyst to prepare a polyorganosiloxane compound represented by Formula 1.

Further, the present invention provides a copolycarbonate resin polymerized with an aromatic diol compound, a carbonate precursor, and a polyorganosiloxane compound represented by Formula 1.

Advantageous Effects

As is apparent from the above, the present invention advantageously provides a polyorganosiloxane compound which may be applied to a variety of applications, and in particular, may be used as an impact modifier, a modifier or a comonomer of a copolycarbonate resin, and a copolycarbonate resin comprising the same and having improved mechanical properties such as low-temperature impact strength while maintaining transparency.

DESCRIPTION OF DRAWINGS

FIG. 1(a) illustrates a $^1$H NMR spectrum of the polyorganosiloxane compound prepared according to Example 1 and FIG. 1(b) illustrates a $^1$H NMR spectrum of the polyorganosiloxane compound prepared according to Example 2.

FIG. 2(a) and FIG. 2(b) illustrate a $^1$H NMR spectrums of polydimethylsiloxane-polycarbonate modified with polyorganosiloxane compounds prepared according to examples; in particular.

BEST MODE

Hereinafter, the present invention will be described in detail.

A polyorganosiloxane compound of the present invention is represented by Formula 1 below:

[Formula 1]

wherein $R_1$, $R_2$, $R_3$, $R'_1$, $R'_2$, and $R'_3$ are independently hydrogen, an alkyl group having a carbon number of 1 to 3, or an aryl group, $R_4$ is $R'_4$ is an alkyl group having a carbon number of 1 to 3, an aryl group, or any one of $R_5$, $R'_5$, and $R_7$ is independently —OH and each of the others is hydrogen, $R_6$ is hydrogen or an alkoxide group having a carbon number of 1 to 4, $R_8$ is a linear or branched alkylene group having a carbon number of 2 to 8, and n and m are integers where $0<n+m\leq 99$.

The polyorganosiloxane compound may be a monomer used as at least one selected from the group consisting of a comonomer, a modifier, and an impact modifier.

As one embodiment, the polyorganosiloxane compound may be a monomer used to prepare a copolycarbonate resin.

As one embodiment, $R_1$, $R_2$, $R_3$, $R'_1$, $R'_2$, and $R'_3$ may each be $CH_3$— or $C_6H_5$—.

As one embodiment, $R_6$ may be hydrogen.

As another embodiment, $R_5$ and $R'_5$ may be hydrogen, and $R_7$ may be —OH.

As another embodiment, since impact strength and fire retardancy of a prepared final product are improved when increasing a chain length of $R_8$, but the glass transition temperature falls when a carbon number of $R_8$ exceeds 8, $R_8$ may be an alkylene having a carbon number of 2 to 8 or an alkylene having a carbon number of 3 to 5, particularly a branched alkylene having a carbon number of 3 to 5.

n is an integer of 10 to 90 or an integer of 25 to 75, m is an integer of 10 to 90 or an integer of 25 to 75, and n+m is 1 to 99 or 50 to 99. Within this range, excellent mechanical properties and transparency may be exhibited.

As a specific embodiment, a compound represented by Formula 1 may be a compound represented by Formula 2 below:

[Formula 2]

wherein p is the same as n+m of Formula 1.

As another embodiment, a compound represented by Formula 1 may be a compound represented by Formula 3 below:

[Formula 3]

wherein p is the same as n+m in Formula 1.

As a specific embodiment, a method of preparing the polyorganosiloxane compound comprises: esterificating hydroxybenzoic acid with an alkenyl alcohol having a carbon number of 2 to 8, as a starting material, to prepare alkenyl hydroxybenzoate; and hydrosilylating the alkenyl hydroxybenzoate with a compound (H-PDMS) having hydrogen terminal groups in both sides thereof as polyorganosiloxane to prepare a polyorganosiloxane compound represented by Formula 1.

As the starting materials, o-hydroxybenzoic acid or p-hydroxybenzoic acid, and an alkenyl alcohol having a carbon number of 2 to 8, may be used. As a specific embodiment, a method of preparing the polyorganosiloxane compound represented by Formula 2 using parahydroxybenzoic acid and an alkenyl alcohol having a carbon number of 2 to 8 may be represented by Reaction Formula 1 below.

[Reaction Formula 1]

A catalyst of Reaction Formula 1 is not specifically limited so long as the catalyst is an acid catalyst which may be used in synthesis of polyorganosiloxane. For example, the catalyst may be at least one selected from the group consisting of $H_2SO_4$, $HClO_4$, $AlCl_3$, $SbCl_5$, $SnCl_4$, and acid white clay.

As one embodiment, the acid catalyst may be used in an amount of 0.1 to 10 parts by weight, 0.5 to 5 parts by weight, or 1 to 3 parts by weight, based on 100 parts by weight of H-PDMS.

As one embodiment, the acid catalytic reaction may be performed for 1 to 6 hours at 50 to 70° C.

As desired, the acid catalytic reaction may be carried out using dioxane, tetrahydrofuran, diethyl ether, diisopropyl ether, diethylene glycol dimethyl ether, a chlorinated hydrocarbon such as dichloromethane, trichloromethane, tetrachloromethane, 1,2-dichloroethane, and trichloroethylene, a hydrocarbon such as pentane, n-hexane, hexane isomer mixtures, heptane, and octane, and aprotic solvents such as solvent naphtha, petroleum ether, benzene, toluene, and xylene, in a range of 1 to 10 times (by weight) based on polyorganosiloxane.

As one embodiment, the hydrosilylation may be carried out in the presence of a metal catalyst.

The metal catalyst is not specifically limited so long as the metal catalyst may be used in modification of polyorganosiloxane terminals, and for example, may be a Pt catalyst.

The Pt catalyst is not specifically limited so long as the Pt catalyst may be used in synthesis of polyorganosiloxane, and, for example, may be at least one selected from the group consisting of an Ashby catalyst, a Karstedt catalyst, a Lamoreaux catalyst, a Speier catalyst, $PtCl_2(COD)$, $PtCl_2$(benzonitrile)$_2$, and $H_2PtBr_6$.

As one embodiment, the metal catalyst may be used in an amount of 0.001 to 1 parts by weight, 0.005 to 0.1 parts by weight, or 0.01 to 0.05 parts by weight, based on 100 parts by weight of the polyorganosiloxane such as H-PDMS.

As desired, the hydrosilylation may be carried out using dioxane, tetrahydrofuran, diethyl ether, diisopropyl ether, diethylene glycol dimethyl ether, a chlorinated hydrocarbon such as dichloromethane, trichloromethane, tetrachloromethane, 1,2-dichloroethane, and trichloroethylene, a hydrocarbon such as pentane, n-hexane, hexane isomer mixtures, heptane, and octane, and aprotic solvents such as solvent naphtha, petroleum ether, benzene, toluene, and xylene, in a range of 1 to 10 times (by weight) based on the polyorganosiloxane such as H-PDMS.

As one embodiment, the hydrosilylation may be carried out for 1 to 5 hours at 60 to 100° C.

A product of Reaction Formula 1 is a compound represented by Formula 2, and a compound designated as a number "5" in Reaction Formula 2 may be generated according to Reaction Formula 2 below.

[Reaction Formula 2]

As another embodiment, the method of preparing polyorganosiloxane may comprise:

reacting H-PDMS with an alkenyl alcohol having a carbon number of 2 to 8, as a starting material, to obtain OH-PDMS; and adding hydroxybenzoic acid to the OH-PDMS and then performing esterification in the presence of an acid catalyst, to prepare a polyorganosiloxane compound represented by Formula 1.

For reference, the term "H-PDMS" means polydimethylsiloxane (PDMS) capped with hydrogen (—H), i.e., H-PDMS-H, so long as it is not specified otherwise. The term "OH-PDMS" means polydimethylsiloxane capped with a hydroxyl group (—OH), i.e., OH-PDMS-OH, so long as it is not specified otherwise.

As a specific embodiment, a preparation method using H-PDMS as the starting material may be represented by Reaction Formula 3 below.

[Reaction Formula 3]

In particular, the polyorganosiloxane compound represented by Formula 1 may be obtained by: reacting H-PDMS with an alkenyl alcohol having a carbon number of 2 to 8, as a starting material, and then performing hydrosilylation; and adding hydroxybenzoic acid to the hydrosilylated product and then performing esterification.

Here, the acid of Reaction Formula 3 is not specifically limited so long as the acid is an acid catalyst which may be used in synthesis of polyorganosiloxane, and a reaction condition is sufficient so long as the reaction may be carried out according to a conventional esterification condition.

As one embodiment, the hydrosilylation may be carried out in the presence of a metal catalyst.

The metal catalyst is not specifically limited so long as the metal catalyst may be used in denaturation of terminals of polyorganosiloxane, and for example, may be a Pt catalyst.

The Pt catalyst is not specifically limited so long as the Pt catalyst may be used in synthesis of polyorganosiloxane, and for example, may be at least one selected from the group consisting of an Ashby catalyst, a Karstedt catalyst, a Lamoreaux catalyst, a Speier catalyst, $PtCl_2(COD)$, $PtCl_2(benzonitrile)_2$, and $H_2PtBr_6$.

As one embodiment, the metal catalyst may be used in an amount of 0.001 to 1 parts by weight, 0.005 to 0.1 parts by weight, or 0.01 to 0.05 parts by weight, based on 100 parts by weight of polyorganosiloxane such as H-PDMS.

As desired, the hydrosilylation may be carried out using dioxane, tetrahydrofuran, diethyl ether, diisopropyl ether, diethylene glycol dimethyl ether, a chlorinated hydrocarbon such as dichloromethane, trichloromethane, tetrachloromethane, 1,2-dichloroethane, and trichloroethylene, a hydrocarbon such as pentane, n-hexane, hexane isomer mixtures, heptane, and octane, and aprotic solvents such as solvent naphtha, petroleum ether, benzene, toluene, and xylene, in a range of 1 to 10 times (by weight) based on polyorganosiloxane such as H-PDMS.

As one embodiment, the hydrosilylation may be carried out for 1 to 5 hours at 60 to 100° C.

A copolycarbonate resin of the present invention is polymerized with an aromatic diol compound, a carbonate precursor, and a polyorganosiloxane compound represented by Formula 1 below:

[Formula 1]

wherein $R_1$, $R_2$, $R_3$, $R'_1$, $R'_2$, and $R'_3$ are independently hydrogen, an alkyl group having a carbon number of 1 to 3, or an aryl group, $R_4$ is $R'_4$ is an alkyl group having a carbon number of 1 to 3, an aryl group, or, any one of $R_5$, $R'_5$, and $R_7$ is independently —OH and each of the others is hydrogen, $R_6$ is hydrogen or an alkoxide group having a carbon number of 1 to 4, $R_8$ is a linear or branched alkylene group having a carbon number of 2 to 8, and n and m are integers where $0<n+m\leq99$.

As one embodiment, the copolycarbonate resin is polymerized with 25 to 85 wt % of the aromatic diol compound, 1 to 60 wt % of the polyorganosiloxane compound represented by Formula 1, and 10 to 70 wt % of the carbonate precursor, based on a total weight of 100 wt % of a mixture comprising the aromatic diol compound, the carbonate precursor, and the polyorganosiloxane compound represented by Formula 1.

Within this range, low-temperature impact strength is maintained and excellent transparency is exhibited compared to one having a similar molecular weight.

As another embodiment, the polycarbonate may be polymerized with 30 to 70 wt % of the aromatic diol compound, 5 to 50 wt % of the polyorganosiloxane compound represented by Formula 1, and 20 to 60 wt % of the carbonate precursor, based on a total weight of 100 wt % of a mixture comprising the aromatic diol compound, the carbonate precursor, and the polyorganosiloxane compound represented by Formula 1.

The aromatic diol compound, for example, may be at least one selected from the group consisting of bis(4-hydroxyphenyl)methane, bis(4-hydroxyphenyl)ether, bis(4-hydroxyphenyl)sulfone, bis(4-hydroxyphenyl)sulfoxide, bis(4-hydroxyphenyl)sulfide, bis(4-hydroxyphenyl)ketone, 1,1-bis(4-hydroxyphenyl)ethane, 2,2-bis(4-hydroxyphenyl)propane (bisphenol A), 2,2-bis(4-hydroxyphenyl)butane, 1,1-bis(4-hydroxyphenyl)cyclohexane (bisphenol Z), 2,2-bis(4-hydroxy-3,5-dibromophenyl)propane, 2,2-bis(4-hydroxy-3,5-dichlorophenyl)propane, 2,2-bis(4-hydroxy-3-bromophenyl)propane, 2,2-bis(4-hydroxy-3-chlorophenyl)propane, 2,2-bis(4-hydroxy-3-methylphenyl)propane, 2,2-bis(4-hydroxy-3,5-dimethylphenyl)propane, 1,1-bis(4-hydroxyphenyl)-1-phenylethane, bis(4-hydroxyphenyl)diphenylmethane, and α,ω-bis[3-(o-hydroxyphenyl)propyl]polydimethylsiloxane, preferably bisphenol A. In this case, the flow of a resin is increased.

As one embodiment, the carbonate precursor is a compound represented by Formula 4 below:

[Formula 4]

wherein $X_1$ and $X_2$ are independently a halogen, a haloalkyl group, a halocycloalkyl group, a haloaryl group, an alkoxy group, or a haloalkoxy group. Within this range, intrinsic characteristics of the polycarbonate resin are provided.

As one embodiment, the polycarbonate may further comprise a molecular weight regulator for polymerization.

As one embodiment, the molecular weight regulator may be mono-alkylphenol.

The mono-alkylphenol is at least one selected from the group consisting of, for example, p-tert-butylphenol, p-cumylphenol, decylphenol, dodecylphenol, tetradecylphenol, hexadecylphenol, octadecylphenol, eicosylphenol, docosylphenol, and triacontylphenol, and is preferably p-tert-butylphenol. In this case, molecular weight may be effectively regulated.

As one embodiment, the molecular weight regulator may be present in an amount of 0.01 to 10 parts by weight, 0.1 to 6 parts by weight, or 1 to 5 parts by weight, based on 100 parts by total weight of a mixture comprising the aromatic diol compound, the carbonate precursor, and the polyorganosiloxane compound represented by Formula 1. Within this range, a target molecular weight may be obtained.

As one embodiment, the polycarbonate has a glass transition temperature of 145 to 160° C., or 145 to 155° C., and a weight average molecular weight of 10,000 to 80,000 g/mol, 15,000 to 80,000 g/mol, 20,000 to 60,000 g/mol, or 22,000 to 55,000 g/mol. Within this range, low-temperature impact strength is maintained, and at the same time, excellent transparency is exhibited compared to one having similar molecular weight.

As one embodiment, a method of preparing the copolycarbonate resin of the present invention may be an interfacial polymerization method. In this case, polymerization may be carried out at normal pressure and at a low temperature, and a molecular weight may be easily regulated.

As one embodiment, the interfacial polymerization may be carried out by reacting an aromatic diol monomer, a carbonate precursor, and a molecular weight regulator in the presence of an acid binder and an organic solvent.

As one embodiment, the interfacial polymerization method may comprise adding a coupling agent after prepolymerization and then polymerizing again. In this case, a copolycarbonate resin having a high molecular weight may be obtained.

Other materials used in the interfacial polymerization are not specifically limited so long as the materials may be used in polymerization of copolycarbonates, and a use amount thereof may be controlled as necessary.

The acid binder is, for example, an alkali metal hydroxide such as sodium hydroxide, potassium hydroxide, and the like, or an amine compound such as pyridine and the like.

The organic solvent is not specifically limited so long as the organic solvent may be used in conventional copolycarbonate polymerization, and, for example, may be a halogenated hydrocarbon such as methylene chloride, chlorobenzene, and the like.

As one embodiment, the interfacial polymerization may further use a reaction accelerator such as a tertiary amine compound, a quaternary ammonium compound, a quaternary phosphonium compound, and the like such as triethylamine, tetra-n-butylammoniumbromide, tetra-n-butylphosphonium bromide, and the like.

The interfacial polymerization may be carried out, for example, for 10 minutes to 5 hours at 0 to 40° C., and pH during reaction is preferably maintained at, for example, 9 or more, or 11 or more.

As one embodiment, the molecular weight regulator may be added before polymerization initiation, during polymerization initiation, or after polymerization initiation.

A molding product according to the present invention is characterized by comprising the copolycarbonate resin. The molding product, for example, may be an injection molding product.

The molding product may further comprise, for example, at least one selected from the group consisting of an antioxidant, a plasticizer, an antistatic agent, a nucleating agent, a fire retardant, a lubricant, an impact modifier, a fluorescent brightening agent, an ultraviolet absorbent, a pigment, and a dye.

As one embodiment, a method of preparing the molding product may comprise preparing a pellet by mixing the copolycarbonate resin according to the present invention and an additive such as an antioxidant using a mixer and then extrusion molding a resulting mixture using an extruder, and injecting a dried pellet using an injection molding machine after drying the pellet.

Hereinafter, preferred examples will be provided for better understanding of the present invention. It will be apparent to those skilled in the art that these examples are only provided to illustrate the present invention, and various modifications and alterations are possible within the scope and technical range of the present invention. Such modifications and alterations fall within the scope of claims included herein.

Example 1

Preparation of Compound Designated as No. 4 in Reaction Formula 2 Below 40 g of 4-acetoxybenzoic acid (222 mmol) was added to a 500 ml round bottom flask and was then dissolved in methylene chloride. Subsequently, 31 g of oxalyl chloride (244 mmol) and 1 to 5 drops of DMF were added thereto and then reacted for 3 hours or more. Reaction termination was confirmed using thin layer chromatography (TLC). When the reaction was finished, a material, in which a hydroxyl group of 4-acetoxybenzoic acid was chlorinated, was obtained by evaporation.

The resulting material was added to a flask containing 16.0 g of 2-methallyl alcohol (220 mmol) and 44 g of triethylamine (TEA) (444 mmol) dissolved in ethyl acetate, and was then reacted. Subsequently, a reacted product was filtered and then the filtered solution was evaporated.

Figure 1:
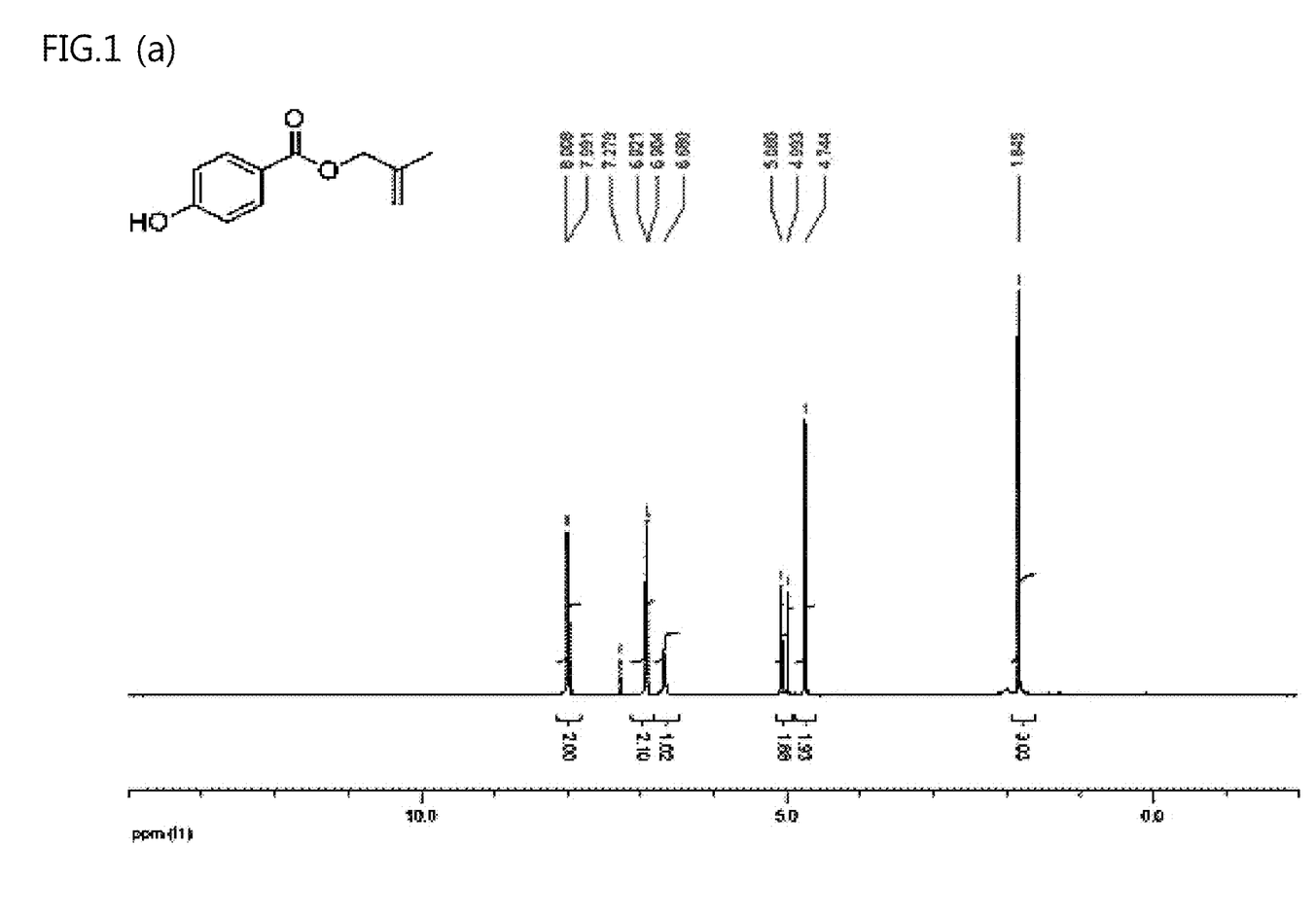
FIG. 1(a) and FIG. 1(b) illustrate a $^1$H NMR spectrum of polyorganosiloxane compounds prepared according to examples; in particular.

A material remaining after evaporation was dissolved in methyl alcohol (MeOH), and then 12.6 g of sodium methoxide (233 mmol) was added thereto. A resulting mixture was reacted for 1 hour or more. After finishing the reaction, the mixture was filtered using an ion exchange resin and was then purified through a column. As a result, a compound designated as No. 4 in Reaction Formula 2, namely, methallyl hydroxybenzoate, was obtained in an amount of 30.8 g. A structure of obtained methallyl hydroxybenzoate was confirmed through $^1$H NMR (see FIG. 1 (a) below).

<Preparation of Polyorganosiloxane Compound (Corresponding to Compound Designated as No. 5 in the Reaction Formula 2) of Formula 1>

47.60 g of octamethylcyclotetrasiloxane (160 mmol) and 2.40 g of tetramethyldisiloxane (17.8 mmol) were mixed. A resulting mixture was reacted with 1 part by weight of an acid white clay (DC-A3) based on 100 parts by weight of octamethylcyclotetrasiloxane in a 3 L flask for 4 hours at 60° C. After reaction termination, a resulting product was diluted with ethyl acetate and then rapidly filtered through celite, resulting in unmodified polyorganosiloxane. A repeat number (p) of the unmodified polyorganosiloxane was 55 when confirmed with $^1$H NMR.

6.9 g of methallyl hydroxybenzoate (36 mmol) as a compound designated as No. 4 in Reaction Formula 2 above and 0.01 g of a Karstedt platinum catalyst (50 ppm) were added to the polyorganosiloxane, a terminal of which was unmodified, and then reacted at 90° C. for 3 hours. After reaction termination, unreacted siloxane was removed by evaporating at 120° C. at 1 torr.

Figure 2:
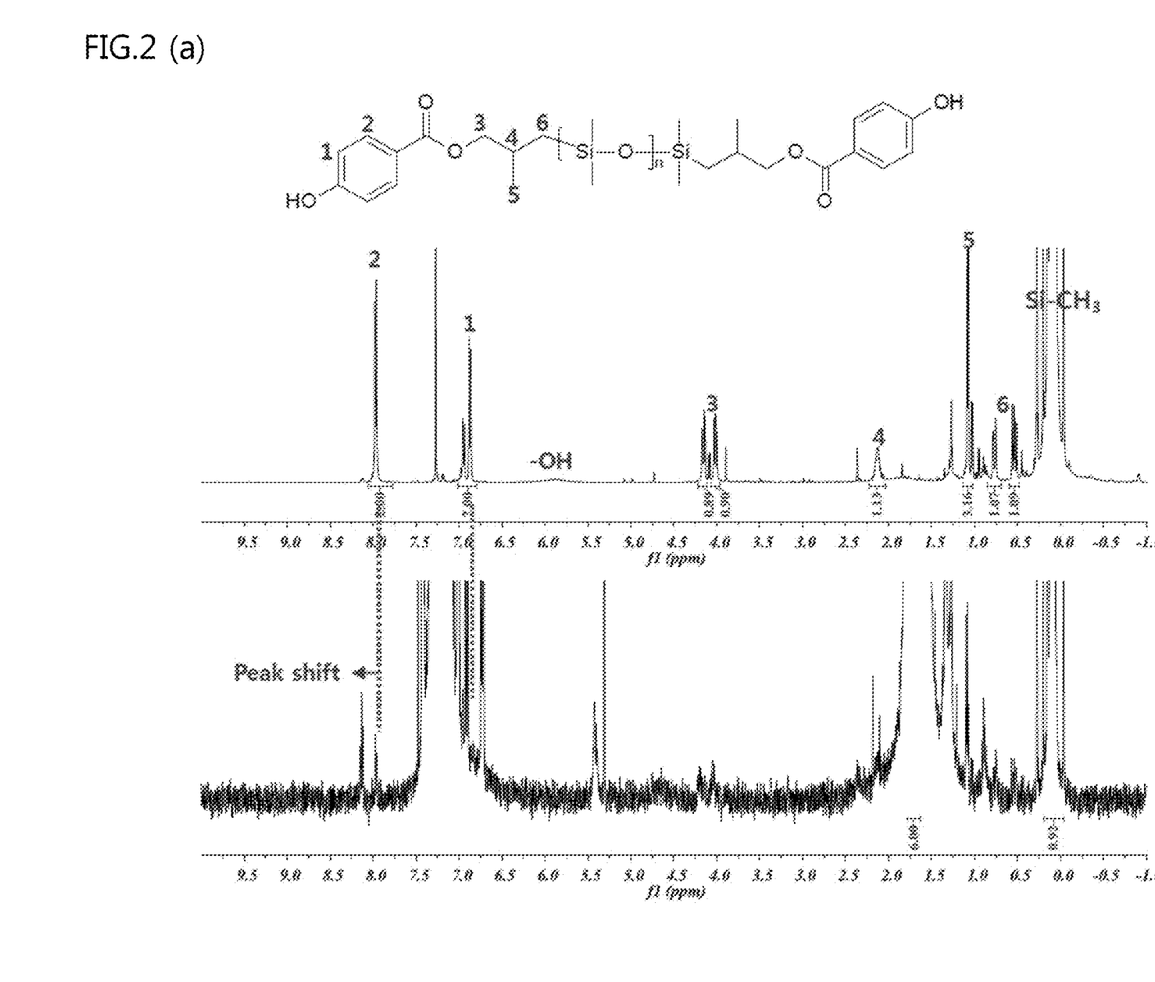
FIG. 2(a) illustrates that modified with Example 1 and FIG. 2(b) illustrates that modified with Example 2.

The polyorganosiloxane, a terminal of which was modified, obtained according to the method above, namely, the polyorganosiloxane compound designated as No. 4 in Reaction Formula 2, was a watery yellow oil, had a repeat number of 55, and did not require additional purification. A structure of the prepared polyorganosiloxane compound designated as No. 5 in Reaction Formula 2 was confirmed with $^1$H NMR (see FIG. 2 (a) below).

Example 2

Preparation of Compound Designated as No. 4 in Reaction Formula 4 Below structure of the prepared polyorganosiloxane compound designated as No. 5 in Reaction Formula 4 was confirmed with $^1$H NMR (see FIG. 2 (b) below).

Comparative Example 1

An experiment was repeated in the same manner as in Example 1, except that 4.81 g of 2-allylphenol was used instead of 6.9 g of methallyl hydroxybenzoate (36 mmol), which was used in the section <Preparation of polyorganosiloxane compound of Formula 1> of Example 1, obtained as An experiment was repeated in the same manner as in Example 1, except that, in the section <Preparation of compound designated as No. 4 in Reaction Formula 2> of Example 1, 19.1 g of 2-methyl-1-butenol (222 mmol) was added instead of 16.0 g of 2-methallyl alcohol (222 mmol).

As a result, 29.1 g of methylbutene hydroxybenzoate as a compound designated as No. 4 in Reaction Formula 4 was obtained. A structure of an obtained methylbutene hydroxybenzoate was confirmed with $^1$H NMR (see FIG. 1 (b) below).

In addition, an experiment was repeated in the same manner as in Example 1, except that 6.13 g of methylbutene hydroxybenzoate (29.7 mmol) obtained as the compound designated as No. 4 in Reaction Formula 4 was used instead of 6.9 g of methallyl hydroxybenzoate (36 mmol), which was used in the section <Preparation of polyorganosiloxane compound of Formula 1> of Example 1, obtained as the compound designated as No. 4 in Reaction Formula 2.

The polyorganosiloxane, a terminal of which was modified, obtained according to the method above, namely, the polyorganosiloxane compound designated as No. 4 in Reaction Formula 3, was a watery yellow oil, had a repeat number of 45 in PDMS, and did not require additional purification. A the compound designated as No. 4 in Reaction Formula 2. In addition, instead of the compound designated as No. 3 in Reaction Formula 2, a siloxane compound (AP-PDMS), both terminals of which were modified with allyl phenol, represented by Formula 5 below, and having a repeat number of 40 in PDMS, was obtained.

[Formula 5]

Comparative Example 2

An identical experiment was repeated in the same manner as in Example 1, except that 4.87 g of eugenol was used instead of 6.9 g of methallyl hydroxybenzoate (36 mmol), which was used in the section <Preparation of polyorganosiloxane compound of Formula 1> of Example 1, obtained as the compound designated as No. 4 in Reaction Formula 2. In addition, instead of the compound designated as No. 3 in Reaction Formula 2, a siloxane compound (EG-PDMS), both terminals of which were modified with eugenol, represented by Formula 6 below, and having a repeat number of 43 in PDMS, was obtained.

[Formula 6]

Experimental Example

Preparation of Copolycarbonate Resin

A copolycarbonate resin and an injection specimen comprising each of the siloxane compounds of Examples 1 and 2 and Comparative Examples 1 and 2 were prepared as follows.

1784 g of water, 385 g of NaOH, and 232 g of bisphenol A (BPA) were added to a polymerization reactor and were then dissolved while mixing under a $N_2$ atmosphere. 4.3 g of p-tert butylphenol (PTBP) and 13.1 g of the siloxane compound obtained according to each of Examples 1 and 2, and Comparative Examples 1 and 2, which was dissolved in methylene chloride (MC), were added thereto. Subsequently, 128 g of triphosgene (TPG) was dissolved in MC, and then a dissolved TPG solution was added thereto and reacted therewith for 1 hour while maintaining pH of the TPG solution at 11 or more. After 10 minutes, 46 g of triethylamine (TEA) was added thereto and thereby a coupling reaction occurred.

After a total reaction time of 1 hour and 20 minutes, pH was lowered to 4 to remove TEA, and then pH of a generated polymer was adjusted to neutral pH, i.e. pH 6 to 7, by cleaning three times with distilled water. A resulting polymer was obtained by reprecipitating in a mixture of methanol and hexane, and then dried at 120° C. to obtain a final copolycarbonate resin.

A molecular weight of the obtained copolycarbonate resin was measured via GPC using a PC Standard. Results are summarized in Table 1 below.

<Preparation of Injection Specimen>

0.050 parts by weight of tris(2,4-di-tert-butylphenyl)phosphite were added to the prepared copolycarbonate resin and then pelletized using a HAAKE Mini CTW twin-screw extruder. Subsequently, a specimen was prepared by injection molding in a 320° C. cylinder and a 90° C. metallic mold, using a HAAKE Minijet injection molding machine.

<Test Items>

Characteristics of an injection specimen of each of the prepared copolycarbonate resins were measured according to methods below. Results are shown in Table 1 below.

Room-temperature impact strength: measured at 23° C. based on ASTM D256 (⅛ inch, Notched Izod).
Low-temperature impact strength: measured at −30° C. based on ASTM D256 (⅛ inch, Notched Izod).
Transparency (Haze): measured based on ASTM D1003 after manufacturing disc specimens having a thickness of 1.5 mm and a diameter of 40 mm.
Weight-average molecular weight (g/mol): measured using an Agilent 1200 series and calibrated with PC standard.
Flow (MI): measured based on ASTM D1238 (300° C. and 1.2 kg).
NMR analysis: $^1$H NMR (D solvent: $CDCl_3$) using a Varian 500 MHz.
Glass transition temperature (Tg): measured with a Differential Scanning Calorimeter (DSC) based on ASTM D 3418.

TABLE 1

| Classification | Mw (g/mol) | Room-temperature impact strength (kgf·cm/cm) | Low-temperature impact strength (kgf·cm/cm) | Transparency (%) | MI (g/10 min) | Tg (° C.) |
|---|---|---|---|---|---|---|
| Example 1 | 33,500 | 66.3 | 60.2 | 1.3 | 12 | 148.4 |
| Example 2 | 34,500 | 67.2 | 62.7 | 1.1 | 10 | 147.8 |
| Comparative Example 1 | 31,500 | 56.4 | 17.1 | 0.6 | 30 | 145.3 |
| Comparative Example 2 | 33,600 | 65.1 | 58.6 | 2.1 | 8 | 143.8 |

As shown in Table 1, it can be confirmed that the copolycarbonate resin (Examples 1 and 2) according to the present invention has excellent physical properties, in particular, low-temperature impact strength, when compared to the copolycarbonate resin comprising a conventional siloxane compound modified with allylphenol (Comparative Example 1) and the copolycarbonate resin comprising a conventional eugenol compound (Comparative Example 2).

What is claimed is:

1. A polyorganosiloxane compound represented by Formula 1 below:

[Formula 1]

wherein $R_1$, $R_2$, $R_3$, $R'_1$, $R'_2$, and $R'_3$ are independently hydrogen, an alkyl group having a carbon number of 1 to 3, or an aryl group having a carbon number of 6 or more, $R_4$ is R'$_4$ is an alkyl group having a carbon number of 1 to 3, an aryl group having a carbon number of 6 or more, or any one of R$_5$, R'$_5$, and R$_7$ is independently —OH and each of the others is hydrogen, R$_6$ is hydrogen or an alkoxide group having a carbon number of 1 to 4, R$_8$ is a linear or branched alkylene group having a carbon number of 2 to 8, and n and m are integers where $0 < n+m \leq 99$.

2. The polyorganosiloxane compound according to claim 1, wherein R$_1$, R$_2$, R$_3$, R'$_1$, R'$_2$, and R'$_3$ each are CH$_3$— or C$_6$H$_5$—.

3. The polyorganosiloxane compound according to claim 1, wherein R$_6$ is hydrogen.

4. The polyorganosiloxane compound according to claim 1, wherein R$_5$ and R'$_5$ are hydrogen, and R$_7$ is —OH.

5. The polyorganosiloxane compound according to claim 1, wherein R$_8$ is a branched alkylene having a carbon number of 3 to 5.

6. The polyorganosiloxane compound according to claim 1, wherein the compound represented by Formula 1 is a compound represented by Formula 2 below:

[Formula 2]

wherein p is the same as n+m in Formula 1.

7. The polyorganosiloxane compound according to claim 1, wherein the compound represented by Formula 1 is a compound represented by Formula 3 below:

[Formula 3]

wherein p is the same as n+m in Formula 1.

8. The polyorganosiloxane compound according to claim 1, wherein the compound represented by Formula 1 is a compound represented by Formula 5 below:

[Formula 5]

wherein p is the same as n+m in Formula 1.

9. A method of preparing a polyorganosiloxane compound, which uses an alkenyl alcohol having a carbon number of 2 to 8 and hydroxybenzoic acid as starting materials, and comprising esterificating the alkenyl alcohol having a carbon number of 2 to 8 with the hydroxybenzoic acid to prepare an alkenyl hydroxybenzoate, and hydrosilylating the alkenyl hydroxybenzoate with H-PDMS, terminal groups in both sides of which are hydrogen, as polyorganosiloxane to prepare a polyorganosiloxane compound represented by Formula 1 below:

[Formula 1]

wherein R$_1$, R$_2$, R$_3$, R'$_1$, R'$_2$, and R'$_3$ are independently hydrogen, an alkyl group having a carbon number of 1 to 3, or an aryl group having a carbon number of 6 or more, R$_4$ is R′$_4$ is an alkyl group having a carbon number of 1 to 3, an aryl group having a carbon number of 6 or more, or any one of R$_5$, R′$_5$, and R$_7$ is independently —OH and each of the others is hydrogen, R$_6$ is hydrogen or an alkoxide group having a carbon number of 1 to 4,

R$_8$ is a linear or branched alkylene group having a carbon number of 2 to 8, and n and m are integers where 0<n+m≤99.

10. A method of preparing a polyorganosiloxane compound, which uses an alkenyl alcohol having a carbon number of 2 to 8 and hydroxybenzoic acid as starting materials, and comprising:
reacting the alkenyl alcohol having a carbon number of 2 to 8 with H-PDMS, terminal groups in both sides of which are hydrogen, as polyorganosiloxane to obtain OH-PDMS; and
adding the hydroxybenzoic acid to the OH-PDMS and esterificating in the presence of an acid catalyst to prepare a polyorganosiloxane compound represented by Formula 1 below:

[Formula 1]

wherein R$_1$, R$_2$, R$_3$, R′$_1$, R′$_2$, and R′$_3$ are independently hydrogen, an alkyl group having a carbon number of 1 to 3, or an aryl group having a carbon number of 6 or more, R$_4$ is R′$_4$ is an alkyl group having a carbon number of 1 to 3, an aryl group having a carbon number of 6 or more or any one of R$_5$, R$_5$, and R$_7$ is independently —OH and each of the others is hydrogen, R$_6$ is hydrogen or an alkoxide group having a carbon number of 1 to 4,

R$_8$ is a linear or branched alkylene group having a carbon number of 2 to 8, and n and m are integers where 0<n+m≤99.

11. A copolycarbonate resin polymerized with an aromatic diol compound, a carbonate precursor, and a polyorganosiloxane compound represented by Formula 1 below:

[Formula 1]

wherein R$_1$, R$_2$, R$_3$, R′$_1$, R′$_2$, and R′$_3$ are independently hydrogen, an alkyl group having a carbon number of 1 to 3, or an aryl group having a carbon number of 6 or more, R$_4$ is R′$_4$ is an alkyl group having a carbon number of 1 to 3, an aryl group having a carbon number of 6 or more, or any one of R$_5$, R′$_5$, and R$_7$ is independently —OH and each of the others is hydrogen,

R$_6$ is hydrogen or an alkoxide group having a carbon number of 1 to 4, R$_8$ is a linear or branched alkylene group having a carbon number of 2 to 8, and n and m are integers where 0<n+m≤99.

12. The copolycarbonate resin according to claim 11, wherein the copolycarbonate resin is polymerized in amounts of 25 to 85 wt % of the aromatic diol compound, 1 to 60 wt % of the polyorganosiloxane compound represented by Formula 1, and 10 to 70 wt % of the carbonate precursor, based on 100 wt % of a mixture comprising the aromatic diol compound, the carbonate precursor, and the polyorganosiloxane compound represented by Formula 1.

13. The copolycarbonate resin according to claim 11, wherein the carbonate precursor is a compound represented by Formula 4 below:

[Formula 4]

wherein $X_1$ and $X_2$ are independently a halogen, a haloalkyl group, a halocycloalkyl group, a haloaryl group, an alkoxy group, or a haloalkoxy group.

14. The copolycarbonate resin according to claim 11, wherein the aromatic diol compound is at least one selected from the group consisting of bis(4-hydroxyphenyl)methane, bis(4-hydroxyphenyl)ether, bis(4-hydroxyphenyl)sulfone, bis(4-hydroxyphenyl)sulfoxide, bis(4-hydroxyphenyl)sulfide, bis(4-hydroxyphenyl)ketone, 1,1-bis(4-hydroxyphenyl)ethane, 2,2-bis(4-hydroxyphenyl)propane (bisphenol A), 2,2-bis(4-hydroxyphenyl)butane, 1,1-bis(4-hydroxyphenyl)cyclohexane (bisphenol Z), 2,2-bis(4-hydroxy-3,5-dibromophenyl)propane, 2,2-bis(4-hydroxy-3,5-dichlorophenyl)propane, 2,2-bis(4-hydroxy-3-bromophenyl)propane, 2,2-bis(4-hydroxy-3-chlorophenyl)propane, 2,2-bis(4-hydroxy-3-methylphenyl)propane, 2,2-bis(4-hydroxy-3,5-dimethylphenyl)propane, 1,1-bis(4-hydroxyphenyl)-1-phenylethane, bis(4-hydroxyphenyl)diphenylmethane, and α,ω-bis[3-(o-hydroxyphenyl)propyl]polydimethylsiloxane.

15. The copolycarbonate resin according to claim 11, wherein the copolycarbonate resin further comprises a molecular weight regulator for polymerization.

16. The copolycarbonate resin according to claim 15, wherein the molecular weight regulator is mono-alkylphenol.

17. The copolycarbonate resin according to claim 16, wherein the molecular weight regulator is comprised in an amount of 0.01 to 10 parts by weight based on 100 parts by weight of a mixture comprising the aromatic diol compound, the carbonate precursor, and the polyorganosiloxane compound represented by Formula 1.

18. The copolycarbonate resin according to claim 11, wherein the copolycarbonate resin has a weight-average molecular weight of 10,000 to 80,000 g/mol and a glass transition temperature of 145 to 160° C.

* * * * *